United States Patent [19]

Barme

[11] Patent Number: 4,500,512

[45] Date of Patent: Feb. 19, 1985

[54] STABILIZING AGENTS FOR LIVE VIRUSES FOR PREPARING VACCINES, AND STABILIZED VACCINES CONTAINING SAID STABILIZING AGENTS

[75] Inventor: Michel Barme, Paris, France

[73] Assignee: Institut Pasteur, Paris, France

[21] Appl. No.: 375,086

[22] Filed: May 5, 1982

[30] Foreign Application Priority Data

May 13, 1981 [FR] France ................................ 81 09490

[51] Int. Cl.³ .......................................... A61K 39/275
[52] U.S. Cl. ....................................................... 424/89
[58] Field of Search ...................... 424/93, 89; 435/235

[56] References Cited

U.S. PATENT DOCUMENTS 3,686,394 8/1972 Huygelen ............................. 424/89
3,873,421 3/1975 Chagnon ............................ 195/1.3

FOREIGN PATENT DOCUMENTS 0028563   5/1981   European Pat. Off. .
0065905  12/1982   European Pat. Off. .
2076787  10/1971   France .
2215946   8/1974   France .
2424031  11/1979   France .
1049386  11/1966   United Kingdom .
1564998   4/1980   United Kingdom .
1575155   9/1980   United Kingdom .

OTHER PUBLICATIONS

Robin et al., Bull. WHO 44:729–737 (1971)(FR), Study of the Heat Stability of Anti-yellow Fever Vaccine in Samples of Eight Batches from Various Countries.
Finter et al., Dev. Biol. Stand. 36:279–283 (1977), Long Term Storage Studies with a New Stabilized Formulation of Yellow Fever Virus Vaccine.
Finter et al., Dev. Biol. Stand. 41:271–276 (1978), Effects of Adverse Storage on Live Virus Vaccines.
Burfoot et al., J. Biol. Stand. 5:173–179 (1977), The Thermal Stability of a Stabilized 17–D Yellow Fever Vaccine, ("Arilvax", Wellcome Fnon, Ltd.).
Lucasse et al., J. Biol. Stand. 6:1–11 (1978), Influence of Various Temperatures in Relation to Time on 17–D Yellow Fever Virus Vaccines.
Tannock et al., J. Biol. Stand. 8:23–34 (1980), The Development of an Improved Experimental Yellow Fever Vaccine (Stabilized Protein-Free).
Moss-Blundell et al., J. Biol. Stand. 9:445–452 (1981), A Clinical Study of Stabilized 17–D Strain Live Attenuated Yellow Fever Vaccine (Arilvax, Wellcome).
Peetermans, J., "Stability of Freeze-dried and Reconstituted Measles Vaccines", *Develop. Biol. Standards*, vol. 41, pp. 259–264, (1978).
McAleer, W. J. et al., "Stability on Storage at Various Temperatures of Live Measles, Mumps and Rubella Virus Vaccines in New Stabilizer", *Journal of Biological Standardization*, 8, 281–287 (1980).
Finter, N. B., et al., "Long Term Storage Studies with a New Stabilized Formulation of Yellow Fever Virus Vaccine", *Develop. Biol. Standard*, vol. 36, pp. 279–283 (1977).

*Primary Examiner*—Shep K. Rose
*Attorney, Agent, or Firm*—Browdy and Neimark

[57] ABSTRACT

The stabilizing agent is constituted by a phosphate buffer solution (PBS) containing calcium and magnesium ions, which contains in addition lactose, sorbitol and at least one amino acid taken from the group which comprises histidine, alanine, valine, threonine, arginine, methionine, hydroxyproline, lysine, isoleucine, phenylalanine, serine, and preferably constituted by an association of histidine and alanine. The stabilized vaccine is constituted by a suspension of live attenuated viruses in the above stabilizing agent, and lyophilized. The invention also relates to the method for preparing such a stabilized vaccine, to the stabilized vaccines so-obtained and to their use for treating viral diseases in humans or animals.

3 Claims, 2 Drawing Figures 4,500,512

STABILIZING AGENTS FOR LIVE VIRUSES FOR PREPARING VACCINES, AND STABILIZED VACCINES CONTAINING SAID STABILIZING AGENTS

BACKGROUND OF THE INVENTION

The present invention relates to a novel stabilizing agent for live viruses, for use of the latter as vaccines and to the stabilized vaccines so-obtained.

Vaccination by inactivated antigens or attenuated live virus strains, have long been used to protect men and animals against viral diseases. In both cases, it is imperative for the integrity of the viral antigens to be preserved in the vaccines in order that the vaccinating effect of the latter may be effective after preparation, storage and transportation of the vaccines to the places of vaccination. Now live attenuated vaccines are particularly fragile and their vaccinating action is rapidly destroyed when they are exposed to temperatures above +4° C. and sometimes even below. Such instability of the vaccines is unacceptable, particularly when these vaccines are used, like anti-yellow fever vaccine, on a large scale in tropical countries where they may accidentally be exposed to high ambient temperatures which are prevailing in these regions, before being administered, considering that the maintenance of the stability of the titer of the live vaccines is the primordial factor for ensuring effective immunization of the vaccinated populations, particularly in regions with a hot climate, and especially in cases where the maintenance of a cold storage line from the manufacturing laboratory to the places of utilization may prove to be insufficient or may be interrupted. It is therefore necessary to be able to provide a stable and heat-resistant vaccine, capable of withstanding deterioration when it is stored for long periods and is exposed accidentally to high temperatures. To confer on live vaccines the heat stability indispensable for the maintenance of the entireness of their vaccinating power or infectivity, it has been proposed to prepare these vaccines, particularly vaccines against measles, rubella, mumps, and yellow fever, in lyophilized form. However, even in this stabilized form, these lyophilized live vaccines are still very fragile, to the point that they must be stored at −30° C. and are shipped in solid carbon dioxide (known under the trademark "CARBOGLACE") at −80° C. However, even by complying with these extremely drastic restrictions of storage and shipment, it is not always possible to avoid the vaccines being exposed, in the course of their storage and their shipment, to high temperatures which causes loss of infectivity of these vaccines and hence, their loss of activity, so that the vaccinated populations are not in fact, protected in any way by vaccination by a vaccine which has lost its infectivity. This loss of infectivity (or titer) under the effect of a rise of temperature, has been clearly shown in a study published by the World Health Organisation, 1974, 44,729–737 under the signature of Y. Robin, A. C. Saenz, A. S. Outschoorn and B. Grab, entitled "Study of the heat stability of anti-yellow fever vaccine in samples of eight batches coming from various countries" whence it emerges that vaccinating compositions stabilized by lyophilization lose about 75% of their initial infectivity following storage for 6 months at +5° C. for two weeks at +22° C., and about 95% of their initial infectivity after one week at 37° C. This is the reason why it has been attempted to improve the heat stability of lyophilized live vaccines, by adding stabilizers thereto. Thus, in French Pat. No. 1,548,489 and Special Medicament Patent 7321M, the Recherche et Industrie Therapeutiques R.I.T. Company proposed adding to attenuated live rubella virus, before or after lyophilization, a stabilizing agent constituted by Hanks solution supplemented with casein hydrolysate (if necessary completed with a second stabilizing aqueous solution containing potassium glutamate, saccharose and chloramphenicol). Results relating to the heat stability of vaccines against measles, lyophilized and reconstituted have, moreover, been made public by this company at the 15th Congress of the AISB on vaccinations in underdeveloped countries, held at Guadeloupe in 1978, and published in Develop. biol. Standard. vol. 41, p. 259–264 (S. Karger Ed., Bale, 1978): the experiments reported in this publication show that with the stabilizing agent recommended by the R.I.T. company, the titer loss is 0.30 $\log_{10}$ after two days and 0.70 $\log_{10}$ after one week, for a lyophilized vaccine exposed to a temperature of 41° C. on a water bath for 14 days, then reconstituted with diluant preheated at 41° C., without the reconstitution causing an additional decrease in the titer. It is to be noted that the Hanks solution recommended according to the R.I.T. Patents, is an aqueous solution containing inorganic salts, glucose and phenol red and that the casein hydrolysate is essentially constituted by the following amino acids: glutamic acid, leucine, proline, lysine, valine, tyrosine, methionine, phenylalanine, arginine, and histidine. It has also been proposed (cf. French Pat. No. 2,371,927 in the name of Connaught Laboratories Ltd.) to stabilize a vaccine against poliomyelitis, with a stabilizing aqueous composition containing about 0.3–1.0M of Tris (hydroxy-)aminomethane buffer, about 100 µg/ml of L-cystine and about 0.8 mg/ml of vaccine, of gelatin hydrolysed by an acid, the hydrolysed gelatin being essentially constituted by the following amino acids: glycocoll, alanine, leucine, phenylalanine, tyrosine, serine, proline, hydroxyproline, aspartic acid, glutamic acid, arginine, lysine, tryptophane. French Patent to Merck & Co. No. 2,424,031 describes, as for it, a "vaccine stabilizer" recommended for stabilizing a vaccinating composition in the lyophilized or liquid state (such as virus of measles, of mumps, of rubella, of chicken pox, of poliomyelitis, of hepatitis, of herpes simplex 1 or 2, or of combinations of these viruses) by means of a stabilizing aqueous solution containing hydrolyzed gelatin, a polyalcohol such as sorbitol and a sufficient amount of acid buffer to maintain the pH between about 6.0 and 6.5, which buffer can be phosphate, acetate or citrate buffer. In the "Journal of Biological Standardization" (1980), 8, p. 281–287, W. J. McAleer, H. Z. Markus, A. A. McLean, E. B. Buynak and M. R. Hilleman have reported experiments that they carried out to determine the stability on storage at various temperatures, of live vaccines against measles, mumps and rubella suspended in this novel stabilizing agent. They have shown that the antimeasles lyophilized vaccine loses less than one third of its infectivity when it has been stored for two months at 36°–38° or for one month at 44°–46° C.

SUMMARY OF THE INVENTION

It is an object of the present invention to provide a stabilizing agent for vaccines containing live attenuated viruses, which responds to the necessities of practice better than the stabilizing agents proposed by the prior art, in that it enables stabilized live vaccines to be obtained whose heat stability is distinctly improved, even when these vaccines are subjected to high temperatures for long periods, with respect to that of vaccines stabilized by stabilizing agents proposed in the prior art.

It is another object of the invention to provide stabilizing agents which are simpler in composition than those proposed in the prior art and, consequently, of lower cost price with respect to the latter, thus enabling the production of stabilized vaccines under more favorable economic conditions than in the past.

It is a further object of the invention to provide improved stabilizing agents suitable for use in association with certain viral vaccines whose active components are thermo-sensitive, said vaccines being lyophilizable, as is the case for anti-yellow fever vaccine.

Other objects and advantages of the stabilizing agents, stabilized vaccines, method of preparing stabilized vaccines and methods of treating or preventing viral diseases, according of the invention, will be apparent from the description which follows.

According to the present invention, there is provided a stabilizing agent for vaccines containing live attenuated viruses, characterised in that it is constituted by a phosphate buffer solution (PBS) containing calcium and magnesium ions, which solution contains in addition, lactose, sorbitol and at least one amino acid.

As is known, the composition of the phosphate buffer solution (PBS) containing calcium and magnesium ions which is well known, is as follows:

NaCl: 8 g p. 1000
KCl: 0.2 g p. 1000
$Na_2HPO_4, 2H_2O$: 1.13 g p. 1000
$KH_2PO_4$: 0.2 g p. 1000
$CaCl_2$: 0.1 g p. 1000
$MgSO_4, 7H_2O$: 0.076 g p. 1000
$H_2O$ q.s.p.: 1000 ml

In accordance with the invention, the amount of lactose added to the PBS buffer solution containing calcium and magnesium ions is such that its final concentration in the stabilizing agent according to the invention, is of the order of 4%. The amount of sorbitol added to the $PBS + Ca^{++}$ and $Mg^{++}$ solution is such that its final concentration in the stabilizing agent according to the invention, is of the order of 2% and the amount of amino acid(s) added to the $PBS + Ca^{++}$ and $Mg^{++}$ solution is such that the final concentration of amino acid(s) in the stabilizing agent according to the invention is of the order of 0.005M to 0.05M.

The amino acid or amino acids applied in the stabilizing agent according to the invention, are selected preferably from among amino acids soluble under the conditions of preparing the vaccines, and especially, from the group which comprises histidine, alanine, valine, threonine, arginine, methionine, hydroxyproline, lysine, isoleucine, phenylalanine, and serine.

According to a preferred embodiment of the stabilizing agent according to the invention, the latter contains histidine and alanine, each at a final concentration of 0.01M.

It is also an object of the present invention to provide stabilized vaccines containing attenuated live viruses, characterised in that the vaccine is essentially constituted by a suspension of live attenuated viruses in the stabilizing agent according to the invention, whose composition has been defined above, and then lyophilized.

According to another aspect of the invention there is provided a method for the preparation of stabilized vaccines containing attenuated live viruses, characterised in that a concentrated preparation of attenuated live vaccine, is suspended in a suitable amount of a stabilizing agent solution, as defined above, after which the suspension so-obtained is lyophilized, the pellets of lyophilized vaccine are rehydrated—or reconstituted—at the time of use, by the addition of a suitable amount of distilled water.

In this manner attenuated live vaccines are obtained whose heat stability is particularly remarkable and of which the loss of infectivity is extremely low even when they are subjected to temperatures of the order of 40° C., which permits the use of these stabilized vaccines to be envisaged in temperate or tropical climates even in the accidental or temporary absence of refrigeration means, with excellent reliability as to the protection that they are capable of conferring on the populations to which they are administered.

The stabilized attenuated live vaccines according to the present invention, are essentially vaccines against yellow fever and vaccines against measles, rubella, mumps, influenza and chicken pox.

DESCRIPTION OF A PREFERRED EMBODIMENT

Figure 1:
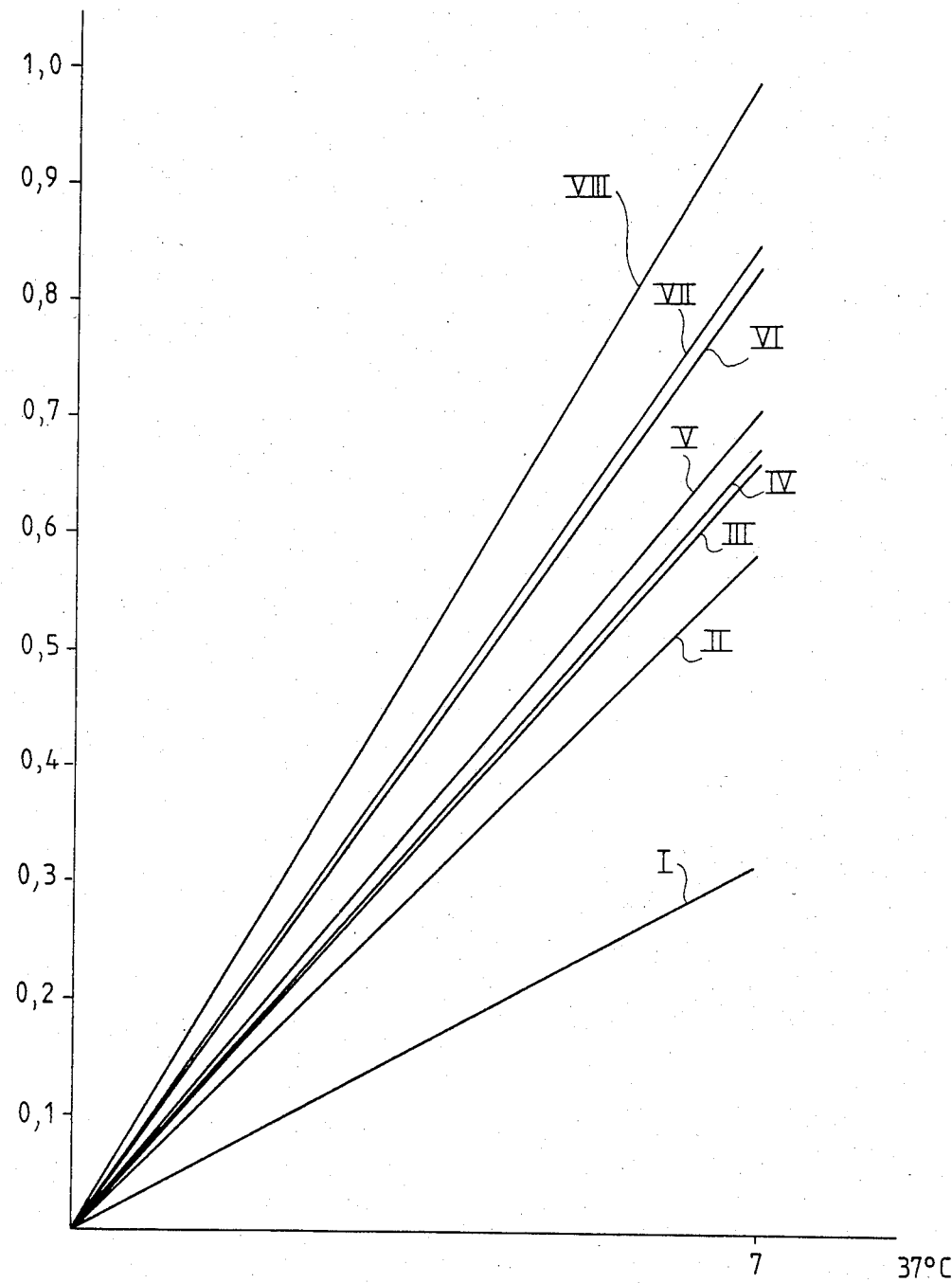

The invention will be described in more detail in the remaining description which follows, with reference to an example of the preparation of a stabilized lyophilized vaccine according to the invention.

It must be well understood, however, that this example of the preparation is given purely by way of illustration of the invention, of which it does not in any way constitute a limitation thereof.

In addition, the heat stability of the stabilized vaccines according to the present invention, has been tested on vaccines against yellow fever, strain 17D, which are particularly fragile vaccines, which are very rapidly destroyed by heat at temperatures as low as +4° C. and even lower. Their heat stability has been, in addition, compared on the one hand with that of lyophilized anti-yellow fever vaccines at present manufactured by Institut Pasteur Production (IPP) and on the other hand with that of a stabilized anti-yellow fever vaccine prepared by the Wellcome Company, which has not disclosed the composition of the stabilizing agent that it incorporates with the lyophilized vaccine that it produces, but has however described the results that it has obtained in "Developp. Biol. Standard.", vol. 36, p. 279-283 (S. Karger Editeur, Bale, 1977).

I

Example of preparation of a stabilized anti-yellow fever vaccine in accordance with the present invention 1°—Preparation of the viruses Embryonized chicken eggs were used which were incubated until the embryo developed, that is to say for about 10 days.

Into the allantoidian cavity there was then innoculated the desired amount of germs of strain 17D of the yellow fever virus; this germ diffuses and infects the eggs, including the embryo thereof.

At the end of 4 days of incubation, the embryos were collected, the feet and head were cut off, they were ground in a helical grinder and the ground material was collected.

2°—Preparation of the stabilizing agent solution

The stabilizing agent solution was prepared by adding to a PBS buffer solution containing $Ca^{++}$ and $Mg^{++}$ ions, lactose, sorbitol and one or several amino acids, to obtain the following composition:

PBS buffer solution containing $Ca^{++}$ and $Mg^{++}$ ions:

NaCl: 8 g p. 1000
KCl: 0.2 g p. 1000
$Na_2HPO_4,2H_2O$: 1.13 g p. 1000
$KH_2PO_4$: 0.2 g p. 1000
$CaCl_2$: 0.1 g p. 1000
$MgSO_4, 7H_2O$: 0.07 g p. 1000
Distilled $H_2O$ q.s.p. 1000 ml
Lactose to obtain the final concentration of 4%
Sorbitol to obtain the final concentration of 2%
Amino acids: final concentration 0.02M 3°—Preparation of lyophilized stabilized vaccine The ground material obtained at 1° was suspended in the stabilizing agent solution as described at 2° to obtain the concentration of 100 g of embryos/100 ml of stabilizing agent solution. This concentrated suspension was deep-frozen to $-60°$ C. and stored at this temperature.

4°—Preparation of injectable ampoules of the stabilized vaccine

The frozen concentrated suspension was thawed, diluted by the stabilizing agent solution as described in 2° above, the dilution ratio being adjusted according to the virus titer of the concentrated suspension. After this dilution the final vaccine was obtained and this was distributed into ampoules and then lyophilized.

At the time of use, each ampoule of lyophilized vaccine receives a volume of distilled water equal to the volume of the liquid vaccine previously introduced into this ampoule: the vaccine is thus "reconstituted" and is ready to be injected.

II

Stability Tests

Applicant has been able to establish that the introduction of sorbitol into the stabilizing agent according to the invention, has the effect of protecting the infectivity of the virus during lyophilization and that the lactose improves the physical cohesion of the vaccine preparation and raises the commencing thawing point of the virus suspension in the stabilizing agent.

Applicant has also been able to establish that the protective effect exerted by the stabilizing solution of the viral preparation is essentially due to the presence of the amino acids and of the $Ca^{++}$ and $Mg^{++}$ ions present in the PBS solution.

Applicant has also been able to establish that the stabilizing mixture associated with the virus in the lyophilized product, facilitates rehydration—or reconstitution—of the latter, for its injection: in fact, although the rehydration of the conventional lyophilized product manufactured at present, for its injection, is difficult to obtain due to the fact of the presence of agregates of organic substances in the lyophilized pellet, this is not the case with the stabilized lyophilized product according to the invention, of which rehydration is easy to obtain considering that it does not contain agregates of organic substances.

The heat stability of an injectable solution of stabilized vaccine has been evaluated with stabilizing agents according to the invention containing various amino acids and expressed by the titer loss, $$\overline{m} \pm \frac{ts}{\sqrt{n}}.$$

at log UFP/ml, of the vaccine after exposing the latter for 14 days to 37° C.

In the above equation:
$\overline{m}$ = average of the values observed for the loss of titer
t = index of the Student test
S = standard deviation
n = number of titrations and
UFP/ml = area forming unit/ml Table 1 below shows the titer loss obtained under these conditions, with a solution of stabilizing agent containing one only of the 11 amino acids tested, at a concentration of 0.01M, the figure in the middle indicating the average value of the titer loss and the two figures which frame it indicating the confidence limits of the means. The eleven amino acids tested were selected for their good solubility in the PBS buffer solution containing $Ca^{++}$ and $Mg^{++}$ ions, under conditions of preparation of the vaccine.

TABLE 1

Evaluation of the titer loss of a vaccine stabilized by a solution of stabilizing agent containing a single amino acid at a concentration 0.01 M

| Amino acid | | Titer loss $\overline{m} \pm \frac{ts}{\sqrt{n}}$ log UFP/ml |
|---|---|---|
| Histidine | (n = 6)* | 0.343  0.438  0.532 |
| Alanine | (n = 7)* | 0.318  0.450  0.581 |
| Valine | (n = 6)* | 0.364  0.459  0.555 |
| Threonine | (n = 7)* | 0.378  0.466  0.553 |
| Arginine | (n = 6)* | 0.340  0.492  0.643 |
| Methionine | (n = 6)* | 0.403  0.502  0.602 |
| Hydroxyproline | (n = 7)* | 0.458  0.551  0.643 |
| Lysine | (n = 7)* | 0.521  0.583  0.644 |
| Isoleucine | (n = 5)* | 0.323  0.591  0.858 |
| Phenylalanine | (n = 6)* | 0.435  0.608  0.780 |
| Serine | (n = 6)* | 0.600  0.716  0.831 |

*n = number of titrations

It emerges from this Table that the titer loss obtained after exposure of a vaccine solution stabilized according to the invention for 14 days at 37° C., was very low for all the amino acids tested and did not exceed, in the worst case, that of isoleucine, 0.858. This Table also shows that the lowest titer losses were obtained respectively with histidine and alanine.

The experiments which are reported below have for this reason been pursued with a stabilizing agent containing either histidine alone at a concentration of 0.01M, or alanine alone at a concentration of 0.01M, or an association of histidine and alanine each at a concentration of 0.01M.

Table 2 below shows the titer losses expressed as log UFP/ml obtained respectively with lyophilized vaccines such as at present commercially available and with vaccines stabilized in accordance with the present invention, exposed for 14 days to a temperature of 37° C.

The products (1) and (2) were prepared by diluting with distilled water, and in suitable proportions, the concentrated viral suspension, so as to obtain the final vaccine ready for lyophilization.

For the products (3), (4) and (5), the concentrated viral suspension, belonging to the same preparation batch, was diluted in the stabilizing agent solution whose composition is indicated in Table 2, before proceeding with the lyophilization of the final product.

TABLE 2

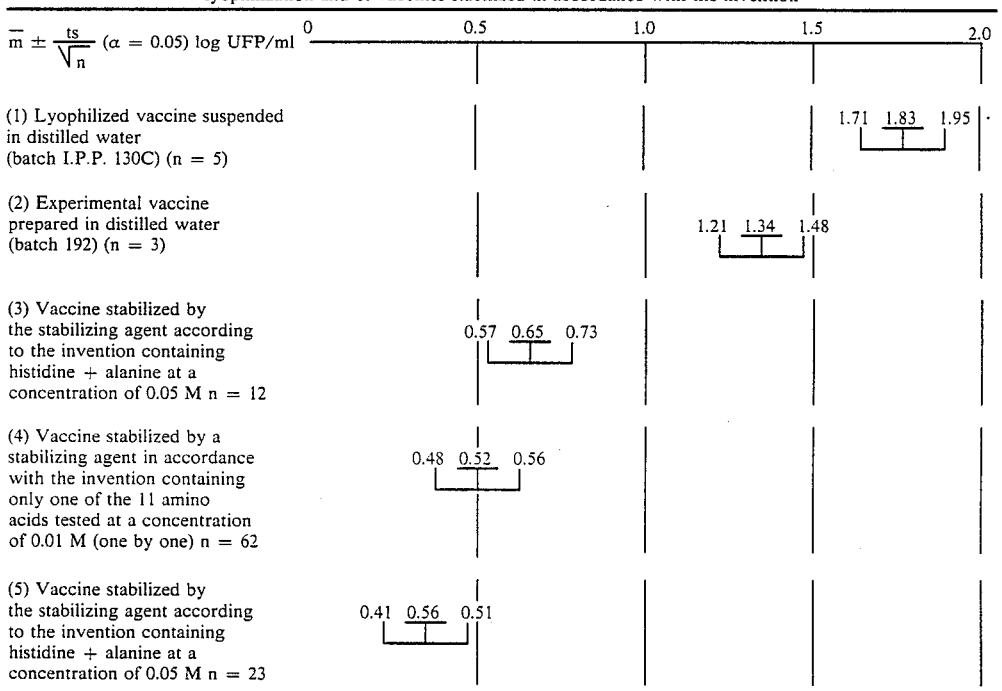

Comparative evaluation of the titer loss of commercial vaccine stabilized by lyophilization and of vaccines stabilized in accordance with the invention

| $\bar{m} \pm \frac{ts}{\sqrt{n}}$ ($\alpha = 0.05$) log UFP/ml | 0 | 0.5 | 1.0 | 1.5 | 2.0 |
|---|---|---|---|---|---|
| (1) Lyophilized vaccine suspended in distilled water (batch I.P.P. 130C) (n = 5) | | | | 1.71 1.83 1.95 | |
| (2) Experimental vaccine prepared in distilled water (batch 192) (n = 3) | | | 1.21 1.34 1.48 | | |
| (3) Vaccine stabilized by the stabilizing agent according to the invention containing histidine + alanine at a concentration of 0.05 M n = 12 | 0.57 0.65 0.73 | | | | |
| (4) Vaccine stabilized by a stabilizing agent in accordance with the invention containing only one of the 11 amino acids tested at a concentration of 0.01 M (one by one) n = 62 | 0.48 0.52 0.56 | | | | |
| (5) Vaccine stabilized by the stabilizing agent according to the invention containing histidine + alanine at a concentration of 0.05 M n = 23 | 0.41 0.56 0.51 | | | | |

It is to be concluded from the Table that the titer loss of a vaccine stabilized according to the invention by means of a stabilizing agent solution containing an association of histidine and alanine each at a concentration of 0.01M, is on the average 3 to 4 times less (according to the batch concerned) than that of a vaccine prepared in distilled water and lyophilized.

The accompanying FIG. 1 shows the graphs of the average loss of titer, expressed in Log UFP/ml, obtained after having exposed for 7 days at 37° C., anti-yellow fever vaccines stabilized by various means, namely:

graph I shows the titer loss of a lyophilized vaccine stabilized by a stabilizing agent according to the invention, containing lactose, sorbitol and, as amino acids: lysine and hydroxyproline, graph II shows the titer loss of a lyophilized vaccine stabilized by sorbitol to which has been added human albumin, graph III shows the titer loss of a lyophilized vaccine stabilized by saccharose, graph IV shows the titer loss of a lyophilized vaccine stabilized by lactose, graph V shows the titer loss of a lyophilized vaccine stabilized by saccharose to which has been added human albumin, graph VI shows the titer loss of a lyophilized vaccine stabilized by a mixture of lactose and sodium glutamate, graph VII shows the titer loss of a lyophilized vaccine stabilized by lactose supplemeted with human albumin, graph VIII shows the titer loss of a vaccine stabilized by lyophilization of a suspension of virus in distilled water.

FIG. 1 demonstrates clearly the remarkable heat stability of the stabilized vaccine in accordance with the present invention.

Figure 2:
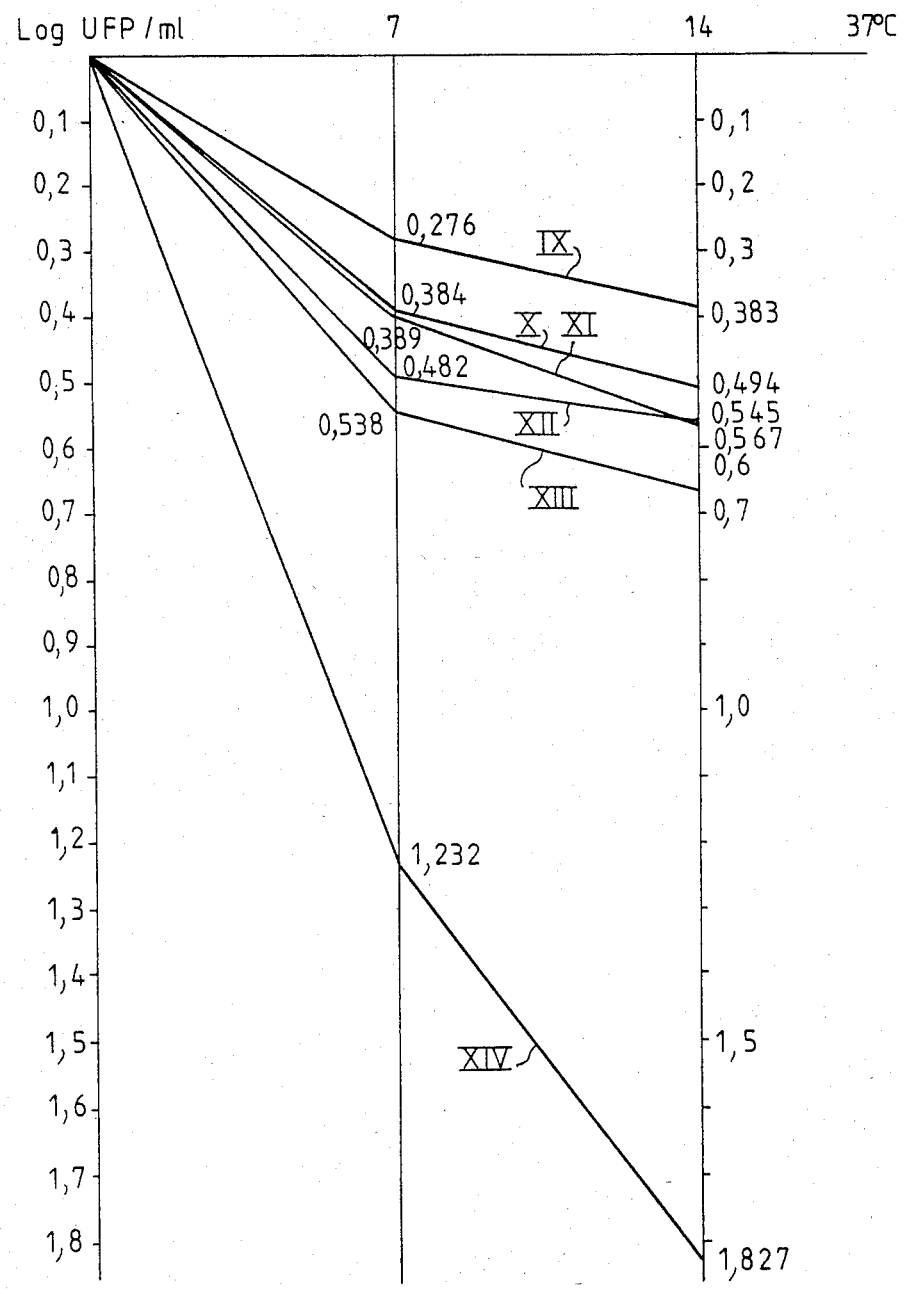

FIG. 2 also attached shows the average titer losses, expressed in Log UFP/ml, noted for 14 days, undergone by lyophilized anti-yellow fever vaccines, stabilized by different stabilizing agents, as well as by an anti-yellow fever vaccine stabilized by simple lyophilization, exposed to a temperature of 37° C., and particularly:

graph IX shows the titer loss undergone by a lyophilized vaccine stabilized in accordance to the invention by a stabilizing agent constituted by PBS+Ca, Mg containing lactose, sorbitol and a mixture of two amino acids at a concentration of 0.01M, graph X shows the titer loss undergone by a lyophilized vaccine stabilized by a stabilizing agent constituted by PBS devoid of Ca++ and Mg++ ions, but containing lactose, sorbitol and two amino acids at a concentration of 0.01M, graph XI shows the titer loss undergone by a lyophilized vaccine stabilized only by a mixture of two amino acids at the concentration of 0.01M.

graph XII shows the titer loss undergone by the Wellcome vaccine mentioned in the aforementioned publication, graph XIII shows the titer loss undergone by a lyophilized vaccine stabilized by a stabilizing agent constituted by PBS devoid of Ca++ and Mg++ ions, but containing lactose, sorbitol and two amino acids at a cocentration of 0.05M, and graph XIV shows the titer loss undergone by a commercial vaccine stabilized by simple lyophilization of an aqueous suspension of the armarillic virus.

Comparison of graphs IX to XIV is unquestionably favorable to the remarkable improvement of the heat stability obtained with the stabilized vaccine in accordance with the present invention.

These results have been confirmed by a comparative heat stability study carried out on batches of anti-yellow fever vaccine 17D resulting from an industrial scale production, diluted respectively with distilled water according to the conventional method, and in a stabilizing agent according to the invention; this comparative study has shown that the vaccine prepared with the stabilizing agent solution according to the invention, has remarkable stability of its infective titer both at 37° C. and at the temperature of the laboratory, with respect to a control stored at −60° C.

This comparative study has been carried out under the following conditions:

Five batches of anti-yellow fever vaccine 17D were prepared and lyophilized in an industrial production plant for this vaccine.

For each of these batches, the same concentrated suspension of virus 17D was divided into two parts. One was diluted with distilled water to obtain the conventional non-thermostable vaccine. The other was diluted with a protective stabilizing agent solution such as defined above. The two portions were then lyophilized simultaneously, in the same operation.

Tables 3 and 4 which follow summarize the results of tests of heat stability at +37° C. and at the temperature of the laboratory (about +20° C.).

The titrations carried out measured the infectious titer of each sample, expressed as log UFP (area forming units). For the test at 37° C., each titration was carried out on three samples introduced in the same series: control stored at −60° C., sample heated to 37° C. for 7 days, sample heated to 37° C. for 14 days. For the test at the temperature of the laboratory, the same technique was applied, titrating simultaneously the following samples: control stored at −60° C., samples kept at ambient temperature for 2 weeks, 1 month, 2 months, 3 months and 6 months. In both cases, the samples subjected to a test and awaiting the day of titration were stored at −60° C.

Tables 3 and 4 show clearly:

(1) that the vaccine prepared by stabilizing has regularly an infectious titer higher than its homolog prepared in distilled water, and that at the level of the control stored at −60° C., outside of any heat test;

(2) that the titer loss was considerably lower with the stabilized vaccine, whatever the temperature and duration of the heat test.

TABLE 3

Anti-yellow fever vaccine
Stability test at the temperature of the laboratory
(Values in log UFP. Averages of 4 titrations)

| Batch no | Vaccine prepared in | Titer loss after exposure to the temperature of the laboratory for: 2 weeks | 1 month | 2 months | 3 months | 6 months |
|---|---|---|---|---|---|---|
| 18 | Distilled water | 0.191 | 0.479 | 0.824 | 0.730 | 1.525 |
| | Stabilizer | 0.116 | 0.127 | 0.167 | 0.233 | 0.274 |
| 25 | Distilled water | — | 0.369 | 0.592 | 0.859 | 1.818 |
| | Stabilizer | — | 0.098 | 0.153 | 0.139 | 1.185 |
| 26 | Distilled water | 0.285 | 0.375 | 0.579 | 0.708 | 0.348 |
| | Stabilizer | 0.125 | 0.208 | 0.263 | 0.336 | 0.504 |
| 27 | Distilled water | 0.225 | 0.411 | 0.655 | 0.826 | 1.329 |
| | Stabilizer | 0.137 | 0.223 | 0.246 | 0.341 | 0.437 |
| 28 | Distilled water | 0.266 | 0.409 | 0.582 | 0.727 | 1.025 |
| | Stabilizer | 0.014 | 0.134 | 0.222 | 0.238 | 0.302 |

TABLE 4

Anti-yellow fever vaccine
Stability test at 37° C.
(titer in log UFP/ml: averages of 4 titrations)

| Batch no | Vaccine prepared in | Control stored at −60° C. | titer loss after heating at 37° C.: 7 days | 14 days |
|---|---|---|---|---|
| 18 | Distilled water | 5.541 | 1.037 | 2.412 |
| | Stabilizer | 5.717 | 0.284 | 0.282 |
| 25 | Distilled water | 5.543 | 0.876 | 1.575 |
| | Stabilizer | 5.875 | 0.140 | 0.148 |
| 26 | Distilled water | 5.357 | 0.730 | 1.090 |
| | Stabilizer | 5.638 | 0.352 | 0.464 |
| 27 | Distilled water | 5.417 | 0.679 | 1.076 |
| | Stabilizer | 5.710 | 0.280 | 0.362 |
| 28 | Distilled water | 5.109 | 0.604 | 0.977 |
| | Stabilizer | 5.426 | 0.237 | 0.292 |

As is shown by the foregoing, the invention is in no way limited to those of its types of application, embodiments and uses which have just been described more explicitly; it encompasses, on the contrary, all modifications which may come to the spirit of the technician skilled in the art, without departing from the framework, or the scope, of the present invention.

What is claimed:

1. Stabilized vaccine containing attenuated live yellow fever virus said attenuated live yellow fever virus being essentially constituted by a suspension of live attenuated yellow fever virus in a stabilizing agent constituted by a phosphate buffer solution (PBS) containing calcium and magnesium ions, about 4% lactose, about 2% sorbitol and aboutn a 0.005M to 0.05M final concentration of at least one amino acid, said stabilized vaccine being lyophilised.

2. Stabilized vaccine according to claim 1, wherein said amino acid is selected from the group consisting of histidine, alanine, valine, threonine, arginine, methionine, hydroxyproline, lysine, isoleucine, phenylalanine, and serine.

3. Stabilized vaccine according to claim 1, wherein said yellow fever virus is strain 17D.

* * * * *